US00PP14919P2

(12) United States Plant Patent
Whetman

(10) Patent No.: US PP14,919 P2
(45) Date of Patent: Jun. 15, 2004

(54) DIANTHUS PLANT NAMED 'DEVON PP 11'

(50) Latin Name: *Dianthus×hybrida*
Varietal Denomination: DEVON PP 11

(76) Inventor: John Whetman, Deer Park Farm, Chudleigh, Devon, TQ13 0NH (GB)

( * ) Notice: Subject to any disclaimer, the term of this patent is extended or adjusted under 35 U.S.C. 154(b) by 0 days.

(21) Appl. No.: 10/676,194

(22) Filed: Sep. 30, 2003

(51) Int. Cl.[7] ..... A01H 5/00

(52) U.S. Cl. ..... Plt./272

(58) Field of Search ..... Plt./272

*Primary Examiner*—Anne Marie Grunberg
*Assistant Examiner*—Annette H Para

(57) ABSTRACT

A new cultivar of Dianthus plant named 'DEVON PP 11' that is characterized by upright, compact habit, grey-green foliage and fragment bi-color flowers that bloom from spring to fall. In combination these traits set 'DEVON PP 11' apart from all other existing varieties of Dianthus known to the inventor.

2 Drawing Sheets

Genus: Dianthus.
Species: ×*hybrida*.
Denomination: DEVON PP 11.

BACKGROUND OF THE INVENTION

The present invention relates to a new and distinct cultivar of carnation that is grown for use as an ornamental landscape and container plant. The new cultivar is known botanically as *Dianthus×hybrid* and will be referred to hereinafter by the cultivar name 'DEVON PP 11'.

'DEVON PP 11' is an induced hybrid plant that is the product of a breeding program started by the inventor in 1980. The breeding program is not federally funded and is on going, conducted in a cultivated area of Houndspool, Dawlish, Devon, United Kingdom. The primary focus of the breeding program is to produce new cultivars of carnations that exhibit unique growth habit. 'DEVON PP 11' was selected in 1996 by the inventor from a large group of open pollinated seedlings, and was selected for height and strongly perfume-scented flowers.

'DEVON PP 11' resulted from the open pollination between the female parent plant Dianthus 'Devon Glow' (unpatented) and the male parent plant which is an unidentified cultivar of Dianthus. 'DEVON PP 11' is distinguishable from the female parent 'Devon Glow' by short flower stalks, bi-colored flowers, upright compact growth habit, early flowering and long flowering season. The closest comparison plant is 'Devon Glow'.

Asexual reproduction of the new cultivar was first accomplished by the inventor in 1986 in a cultivated area of Houndspool, United Kingdom. The method of asexual propagation used was stem cuttings. Since that time the characteristics of the new cultivar have been determined stable and are reproduced true to type in successive generations.

SUMMARY OF THE INVENTION

The following traits have been repeatedly observed and represent the characteristics of the new Dianthus cultivar 'DEVON PP 11'. These traits in combination distinguish this cultivar from all other commercial varieties known to the inventor. 'DEVON PP 11' has not been tested under all possible conditions and phenotypic differences may be observed with variations in environmental, climatic and cultural conditions.

1. Dianthus 'DEVON PP 11' exhibits an upright compact growth habit.
2. Dianthus 'DEVON PP 11' exhibits strongly perfume-scented bi-colored flowers.
3. Dianthus 'DEVON PP 11' is 12 cm. without blooms and 25 cm. in height with blooms, and 30 cm in width.
4. Dianthus 'DEVON PP 11' is a hardy perennial.
5. Dianthus 'DEVON PP 11' blooms early and is long flowering with a blooming season from April to October.
6. Dianthus 'DEVON PP 11' is hardy to minus 15° Centigrade.

BRIEF DESCRIPTION OF THE DRAWINGS

The accompanying color drawings illustrate the overall appearance of the new Dianthus variety 'DEVON PP 11' showing colors as true as it is reasonably possible to obtain in colored reproductions of this type. Colors in the drawings may differ from the color values cited in the detailed botanical description which accurately describe the actual colors of the new variety 'DEVON PP 11'.

The drawing on sheet 1 illustrates the entire plant.

The drawing on sheet 2 illustrates the flower. All drawings were made in June 2003 of plants grown in 1-liter containers in a cold glasshouse in Houndspool, United Kingdom. No chemicals were used to treat the plants. All drawings were made using conventional techniques and although colors may appear different from actual colors due to light reflectance they are as accurate as possible by conventional photography.

BOTANICAL DESCRIPTION OF THE PLANT

The following is a detailed description of the new cultivar 'DEVON PP 11'. Data was collected from plants grown in 1-liter containers indoors in Houndspool, United Kingdom. The color determinations are in accordance with the 2002 edition of The Royal Horticultural Society Color Chart of The Royal Horticultural Society, London, England, except where general color terms of ordinary dictionary significance are used. No chemicals were used to treat the plants. Growing conditions are typical to other Dianthus.

Botanical classification: Dianthus 'DEVON PP 11'.
Species: ×*hybrida*.
Common name: Carnation.
Commercial classification: Hardy perennial.
Use: Ornamental plant for container and landscape.
Parentage: 'DEVON PP 11' is a hybrid plant that resulted from the induced open pollination between the following parent plants:
*Female parent plant.*—Dianthus 'Devon Glow'.
*Male parent plant.*—Unidentified Dianthus cultivar.
Plant description:
*Bloom period.*—April to October.
*Plant habit.*—Upright compact habit.
*Plant height.*—12 cm. when not in bloom and 25 cm. in height when in bloom.
*Plant width.*—30 cm. in width.
*Plant hardiness.*—Hardy to minus 15° Centigrade.
*Type.*—Perennial evergreen herb.
*Root system.*—Fibrous.
*Propagation.*—Propagation is accomplished using stem cuttings.
*Cultural requirements.*—Plant in full sun, well-drained and moderately fertile soil.
*Diseases and pests.*—Susceptible to known Dianthus pests and disease but no other susceptibilities to pests or disease are known to the inventor.
*Time required to produce a rooted plug.*—5 weeks are needed to produce a rooted plug.
*Temperature recommended for cuttings to produce roots.*—The air temperature needed is a minimum of 15° Centigrade air temperature and base heat of 21° Centigrade.
*Crop time.*—6 months is needed to produce a finished 1-liter container size from a rooted plug.
Stem:
*Shape.*—Cylindrical.
*Stem dimensions.*—25 cm. in length and 2–3 mm. in diameter.
*Stem surface.*—Glabrous and glaucous.
*Stem color.*—N189C.
*Branching.*—Numerous basal breaks.
*Internode length.*—4–5 cm. between nodes.
*Node color.*—189D.
*Node dimensions.*—3–4 mm. in diameter and 4 mm. in height.
Foliage:
*Type.*—Evergreen.
*Shape.*—Lanceolate.
*Division.*—Simple.
*Apex.*—Acute.
*Base.*—Decurrent.
*Venation.*—Not Prominent.
*Margins.*—Entire.
*Attachment.*—Sheathing.
*Arrangement.*—Opposite and spiraling up stem.
*Surfaces* (*adaxial and abaxial*).—Glaucous.
*Leaf dimensions.*—95 mm. in length and 4 mm. in width.
*Leaf color* (*adaxial surfaces*).—N189C.
*Leaf color* (*abaxial surfaces*).—N189D.
*Stipules.*—Present.
*Number of stipules.*—2 in number.
*Stipule dimensions.*—7 mm. in length and 2 mm. in width.
*Stipule color.*—189C.
*Fragrance.*—Absent.
Flowers:
*Flower type.*—Salviform, double and symmetrical.
*Flower dimensions* (*including calyx*).—18 mm. in length and 35–50 mm. in diameter.
*Bud color.*—Each individual bud ranges in color from 143B to 143C.
*Bud dimensions.*—6 mm. in length and 22 mm. in width.
*Bud shape.*—Cylindrical.
*Petals.*—Persistant, 15–20 double petals, apopetalous and overlapping.
*Petal margin.*—Dentate (toothed 1–2 mm deep).
*Petal shape.*—Obdeltoid.
*Petal color* (*adaxial surface*).—Colors N74C, 75B and 1D are each individually present on each individual petal.
*Petal color* (*abaxial surface*).—Colors N74C, 75B and 1 D are each individually present on each individual petal.
*Petal surface.*—Glabrous.
*Calyx dimensions.*—6 mm. in width and 18 mm. in length.
*Calyx color.*—Individual calyces range in color from 143B to 143C with anthocyanin often absent.
*Peduncle dimensions.*—3–5 cm. in length and 2–4 mm. in diameter.
*Peduncle color.*—189D.
*Fragrance.*—Strong clove perfume.
*Lastingness of flower.*—Each individual flowers lasts 7–10 days at 20° Centigrade.
Reproductive organs:
*Stamens.*—Ten in number.
*Stamen dimensions.*—25 mm. in length and 1 mm. in diameter.
*Stamen color.*—155A.
*Anther attachment.*—Basifixed.
*Anther shape.*—Ovoid.
*Anther color.*—N74D.
*Pollen.*—Present.
*Amount of pollen.*—Moderate.
*Pollen color.*—In each flower, pollen color ranges from the individual color N74D to the individual color 155A.
*Anther dimensions.*—2 mm. in length and 1 mm. in diameter.
*Pistil.*—Two in number.
*Pistil color.*—In each flower, individual pistil color ranges from 155A to 75D.
*Pistil dimensions.*—12 mm. in length and 1 mm. in width.
*Styles.*—Two in number.
*Style dimensions.*—18–20 mm. in length and 1 mm. in width.
*Style color.*—In each flower individual style color ranges from individual color N74D to the individual color 155A.
*Stigma.*—Single stigma.
*Color of stigma.*—85A.
*Stigma dimensions.*—3–4 mm. in length and 1 mm exserted above petals.
*Ovary position.*—Superior.

*Ovary dimensions.*—7 mm. in length and 4 mm. in diameter.

*Ovary shape.*—Spindle shaped.

*Ovary color.*—145C.

Seed: No seed observed to date.

What is claimed is:

1. A new and distinct cultivar of Dianthus plant named 'DEVON PP 11' as described and illustrated herein.

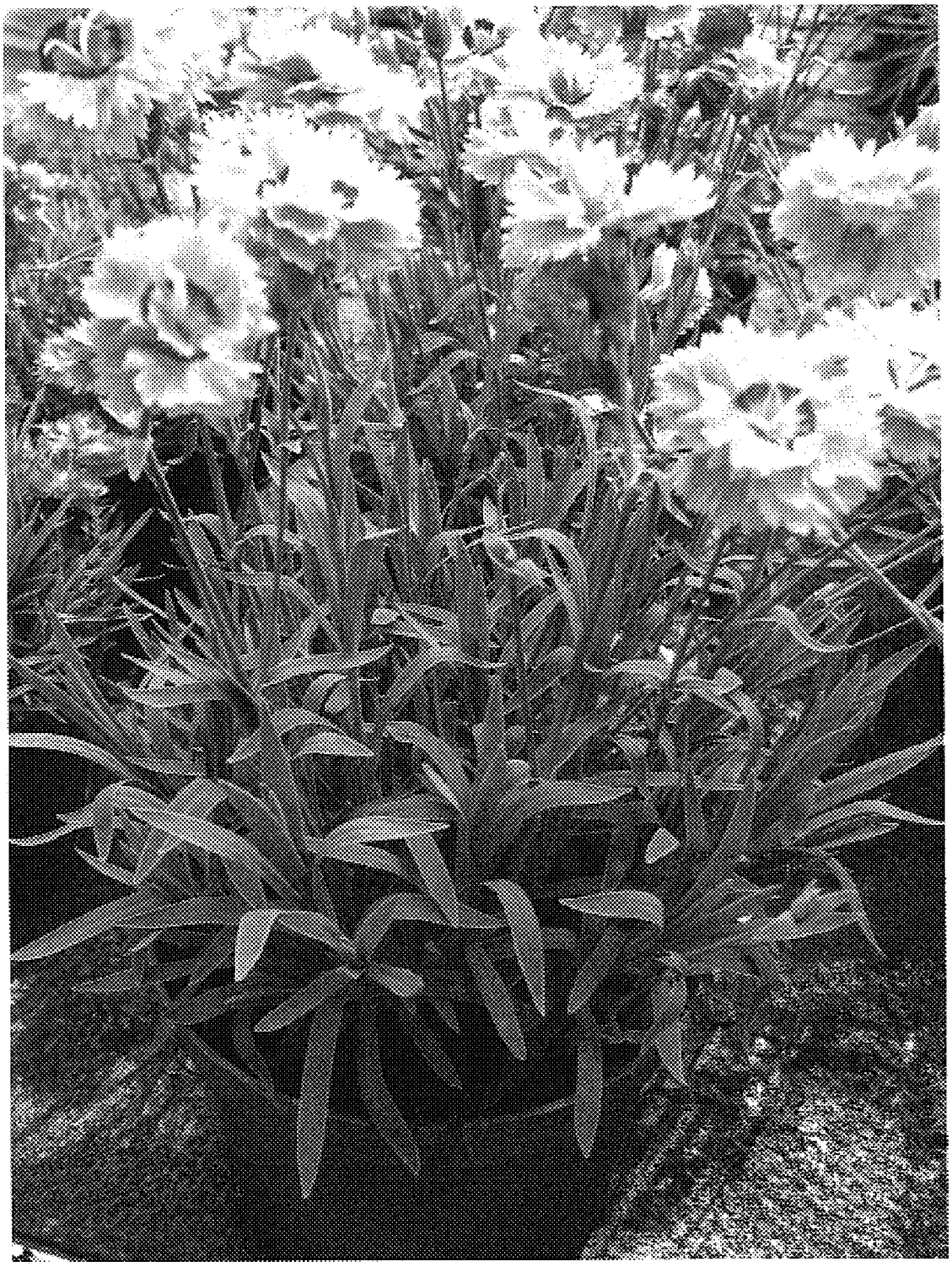

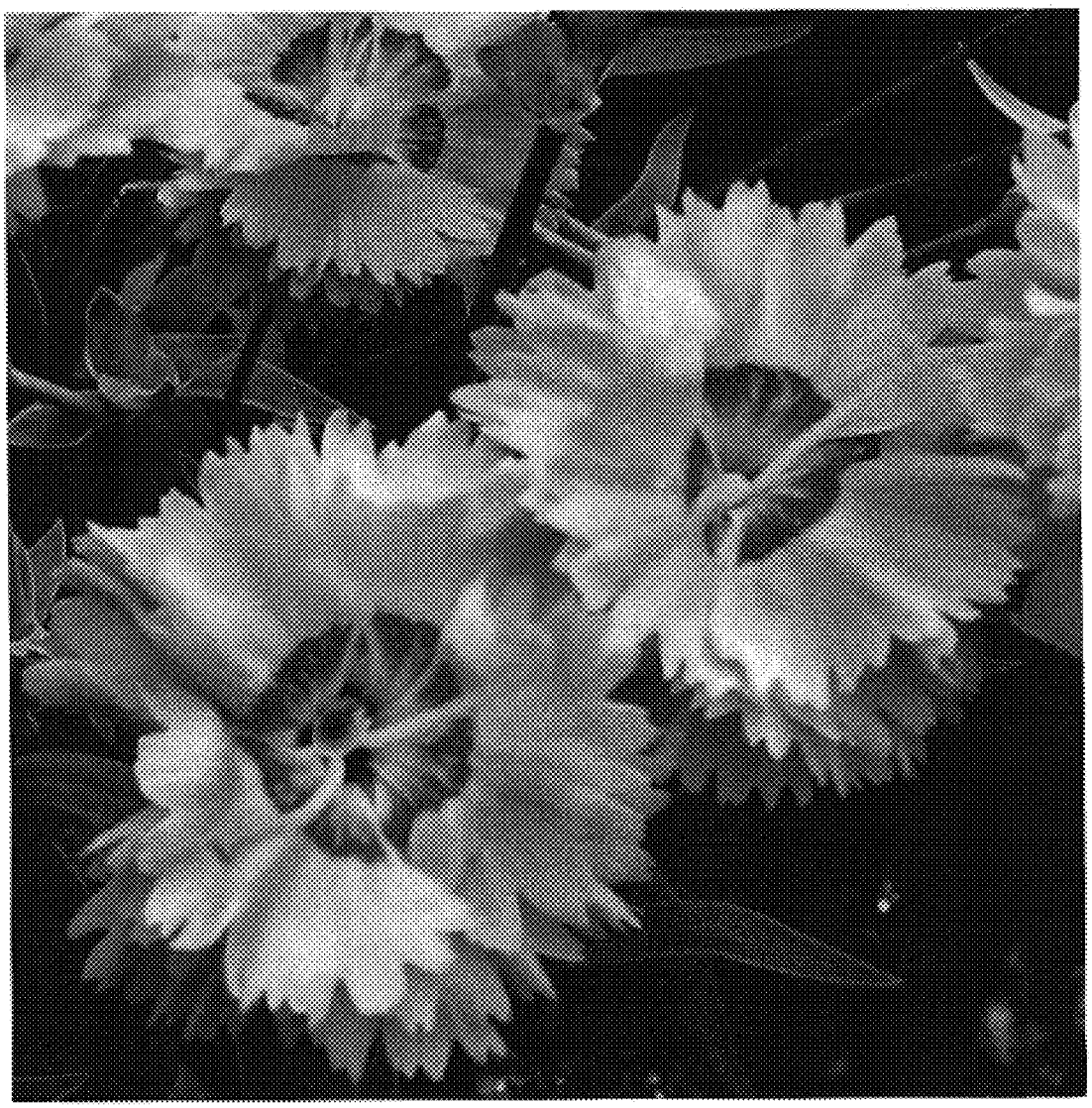

* * * * *